United States Patent
Nguyen

(10) Patent No.: US 7,960,323 B2
(45) Date of Patent: Jun. 14, 2011

(54) NITRATED EXTREME PRESSURE ADDITIVES

(75) Inventor: Duong N. Nguyen, Dover, OH (US)

(73) Assignee: Dover Chemical Corporation, Dover, OH (US)

( * ) Notice: Subject to any disclaimer, the term of this patent is extended or adjusted under 35 U.S.C. 154(b) by 227 days.

(21) Appl. No.: 11/626,502

(22) Filed: Jan. 24, 2007

(65) Prior Publication Data

US 2007/0099803 A1 May 3, 2007

Related U.S. Application Data

(60) Provisional application No. 60/766,581, filed on Jan. 30, 2006.

(51) Int. Cl.
- C10M 133/32 (2006.01)
- C10M 159/18 (2006.01)

(52) U.S. Cl. .................. 508/454; 508/543; 508/549

(58) Field of Classification Search ............. 508/454, 508/491, 549, 543
See application file for complete search history.

(56) References Cited

U.S. PATENT DOCUMENTS

| | | | | |
|---|---|---|---|---|
| 2,192,930 A | * | 3/1940 | Panagiotakos | 508/302 |
| 2,196,101 A | * | 4/1940 | Carmichael et al. | 508/477 |
| 2,340,331 A | * | 2/1944 | Graves et al. | 508/433 |
| 2,696,413 A | * | 12/1954 | Wheildon, Jr. | 384/29 |
| 3,655,556 A | * | 4/1972 | Allen | 508/420 |
| 4,076,738 A | | 2/1978 | Pecoraro | |
| 4,347,148 A | | 8/1982 | Davis | |
| 4,410,746 A | | 10/1983 | Eckler | |
| 4,711,736 A | | 12/1987 | Horodysky et al. | |
| 5,103,061 A | | 4/1992 | Blackborow et al. | |
| 5,144,082 A | * | 9/1992 | Forbus et al. | 568/785 |
| 5,213,697 A | | 5/1993 | Vinci et al. | |
| 5,338,470 A | | 8/1994 | Hiebert et al. | |
| 5,454,842 A | | 10/1995 | Poirier et al. | |
| 5,585,338 A | * | 12/1996 | Beltzer | 508/518 |
| 5,880,072 A | * | 3/1999 | Furey et al. | 508/263 |
| 6,001,782 A | | 12/1999 | Huang | |
| 6,005,144 A | * | 12/1999 | Kropp et al. | 564/485 |
| 6,069,281 A | * | 5/2000 | Kropp et al. | 564/494 |
| 6,362,381 B1 | | 3/2002 | Eiermann et al. | |
| 6,767,872 B2 | * | 7/2004 | Williams | 508/421 |
| 6,888,030 B2 | | 5/2005 | Su et al. | |
| 2001/0037598 A1 | | 11/2001 | Suppes et al. | |
| 2007/0099803 A1 | | 5/2007 | Nguyen | |

FOREIGN PATENT DOCUMENTS

WO WO2007103595 9/2007

OTHER PUBLICATIONS

Polishinskii and Kozlov, "Solubitity of Oil Fraction in Nitro and Chlornitro Derivatives of Low Molecular Weight Alkanes" Chemistry and Technology of Fuels and Oils, ISSN 009-3092 vol. 6 No. 10 Oct. 1970 pp. 730-734.*
Schylapochiniov, "Vibrational Spectrum of Notroethylene", Russian Chemical Bulleting, vol. 17 No. 8 Aug. 1968 pp. 1773-1774.*
International Search Report—Form PCT/ISA210, Aug. 29, 2008.
International Written Opinion—Form PCT/ISA/237, Aug. 29, 2008.

* cited by examiner

*Primary Examiner* — Ellen M McAvoy
*Assistant Examiner* — Pamela Weiss
(74) *Attorney, Agent, or Firm* — Hahn Loeser & Parks LLP

(57) ABSTRACT

This invention relates to processes for making nitro compounds derived from $C_2$-$C_{30}$ unsaturated fatty acids; $C_2$-$C_{30}$ unsaturated fatty oils; esters derived from the reaction of $C_1$-$C_{20}$ alcohols with unsaturated $C_2$-$C_{30}$ fatty acids; $C_2$-$C_{20}$ polyolefins; $C_4$-$C_{20}$ polydiolefins; $C_8$-$C_{20}$ copolymers derived from polyolefins and vinyl aromatics; and $C_4$-$C_{30}$ alkylated phenols using nitric acid or gaseous nitrogen dioxide. This class of extreme-pressure additives was found extremely effective in processing steel, stainless steel and special titanium and nickel or low-iron alloys.

5 Claims, No Drawings

NITRATED EXTREME PRESSURE ADDITIVES

TECHNICAL FIELD

This invention relates generally to the use of nitrated extreme pressure additives and a process for their manufacture.

BACKGROUND OF THE INVENTION

Lubricating oils form interfacial films between moving metallic parts. These oils typically contain one or more of the following additives: boundary additives, corrosion inhibitors, anti-oxidants, dispersants, anti-wear additives, and extreme-pressure ("EP") additives. Boundary, antiwear, and extreme-pressure additives are typically grouped as performance additives while the others as functional additives. This invention pertains to the synthesis and use of nitrated extreme-pressure additives.

Among the performance additives, the primary function of a boundary additive is to reduce friction generated by metal-to-metal rubbing. These additives can be fatty oils, fatty esters, soaps consisting of oxygen-containing functional groups and long-chained hydrocarbons. They are only effective up to temperatures of approximately 150° C. and are therefore effective and useful only for light-duty operations involving soft metals such as copper or aluminum, or light-duty applications involving cast-iron or steel.

For a medium-duty or moderate loads processing steel, low levels of sulfurized additives and/or anti-wear additives such as ZDDP (zinc dithiophosphates), or phosphate esters and phosphites are typically employed. These phosphorous-based compounds are effective up to around 300° C. but lose their effectiveness at higher temperatures.

For heavy-duty applications involving hardened steel, particularly at higher speed and loadings, the extreme-pressure additives such as sulfurized and chlorinated additives have traditionally been employed. These species react with metal surfaces at much higher temperatures ranging from 350° C. for chlorinated additives and from 500° C. for sulfurized additives. Through chemi-adsorption with the metal, these additives form a sacrificial coating to prevent not only wearing, but also welding or adhesion between two dissimilar metal surfaces, such as a die and a work piece.

Presently, commercial extreme-pressure additives contain one or more sulfur, chlorine, or phosphorus-containing compounds. Sulfur-containing additives are sulfurized fat or fatty esters or synthetic polysulfides; chlorine-containing ones are chlorinated paraffins, olefins, or chlorinated fatty compounds; while phosphorus-containing additives consist of phosphate esters and phosphites. Each of the above-mentioned commercial extreme-pressure additives has its own set of limitations.

Sulfurized additives are effective for working with steel parts but not those involving stainless steel or special alloys such as titanium, chromium, or nickel-based, especially those in the most severe working environments. Phosphate esters or phosphites are excellent anti-wear or load-carrying additives but only in light-duty applications. For most cases, they are not effective extreme-pressure additives and definitely unsuitable for applications involving stainless steel. One of the reasons is that these phosphorus and sulfur-containing additives are not very reactive to hardened steel or low-iron metallic composites such as stainless or special alloys mentioned above Chlorinated compounds, on the other hand, are very effective in wide range of metal processing applications involving both steel, stainless steel, and special alloys. The rule of thumb in the industry is that chlorinated additives are required for working with these exotic alloys of low or no iron content. However, recent environmental concern regarding the disposal of chlorinated compounds has prompted the lubricant industry to search for alternatives to replace the chlorinated additive workhorse.

This invention describes a novel class of extreme-pressure additives, labeled generically as "nitrated" or nitro compounds. The nitro compounds cited in this invention can be made by using 70% nitric acid or nitrogen dioxide gas to nitrate many classes of compounds, such as: (1) fatty acids with unsaturation; (2) fatty oils which contain unsaturation sites on their hydrocarbon chains such as vegetable oils, tall oil and animal fats; (3) esters (synthetic or natural) derived from the reaction of alcohols with fatty acids, such as triglycerides; (4) $C_2$-$C_{20}$ polyolefins or $C_4$-$C_{20}$ polydiolefins, more preferably $C_2$-$C_6$ polyolefins containing terminal or internal unsaturation, preferably polyisobutylene (hereinafter referred to synonymously as "PIB"); (5) $C_8$-$C_{20}$ copolymers derived from polyolefins and vinyl aromatics e.g., poly(styrene butadiene); and (6) $C_4$-$C_{30}$ alkylated phenols, e.g., nonyl phenol and wherein the alkyl group is a straight or branched chain.

At least one novel feature of this additive is that it contains nitro-compounds instead of conventional elements such as sulfur, chlorine, or phosphorus, and has demonstrated its effectiveness as an extreme-pressure additive capable of replacing both sulfurized and chlorinated additives for both steel and stainless steel applications, as well as for processing metallic alloys which are currently considered as most challenging such as titanium, nickel, and chromium-based metals or alloys.

U.S. Pat. No. 4,076,738 describes how to make polyisobutylene carboxylic acid by reacting ozonized polyisobutylene with nitric acid for use in the area of fuel and gasoline additives.

U.S. Pat. No. 4,347,148 describes a process of preparing nitro-phenols by reacting polyisobutylene-substituted phenols with nitric acid in presence of sulfuric acid or a Lewis acid. The nitro-phenols were indicated to be useful as fuel dispersants in combustion engines.

U.S. Pat. No. 4,410,746 describes a process preparing nitro-olefins comprising reacting a nitro diol with an aldehyde acceptor in the presence of a catalyst. Such nitro-olefins can be used as solvents or pesticides.

U.S. Pat. No. 5,103,061 describes a nitration process of polyisobutylene ("PIB") using nitrogen oxides gas and subsequent derivatives to generate fuel additives.

U.S. Pat. No. 6,069,281 describes the nitration process of polybutenes or polyisobutylene with nitrogen oxides and further processing with hydrogenation to produce polyamine derivatives for fuel additives.

U.S. Pat. No. 6,362,381 B1 describes the nitration of aromatic hydrocarbons with oxides of nitrogen, an oxygen-containing gas and an oxidic catalyst. The described end use is in the area of fuel additives.

U.S. Pat. No. 6,888,030 B2 describes a process of producing polyamines by hydrogenation of nitrated polyisobutylenes in the presence of a branched alcohol, using 70% nitric acid. The end use for the invented product is fuel additives.

This invention describes a novel class of extreme-pressure additives, labeled generically as "nitrated" compounds. At least one novel feature of this additive is that it contains no or reduced amounts of conventional elements such as sulfur, chlorine, or phosphorus, and has demonstrated its effectiveness as an extreme-pressure additive capable of replacing or partially replacing chlorinated additives for both steel and stainless steel applications.

SUMMARY OF THE INVENTION

An object of this invention is to illustrate a process to produce nitrated fatty additives by nitrating fatty sources such as animal fats, vegetable oils, and the synthetic esters derived therefrom, typically using 70% nitric acid or nitrogen dioxide gas which is the anhydrous form of nitric acid.

Another object of this invention is to illustrate a process to produce nitrated fatty additives from fatty acids such as oleic acid or tall oil fatty acids, using the same nitration method.

Yet another object of this invention is to illustrate a process to produce nitrated additives by nitrating polyalkenes such as polyisobutylene, using 70% nitric acid or nitrogen dioxide gas.

Still yet another object of this invention is to illustrate a process to produce nitrated additives by nitrating terminal or internal olefins, using 70% nitric acid or nitrogen dioxide gas.

A further object of this invention is to illustrate the novel uses of nitro-compounds as new class of extreme-pressure additives which can at least partially replace both sulfurized and chlorinated extreme-pressure additives, and is effective for both regular steel and low-steel or non-steel alloys.

These and other objects of the present invention will become more readily apparent from a reading of the following detailed description taken in conjunction with the appended claims.

DETAILED DESCRIPTION OF THE INVENTION

The nitration process of the instant invention is carried out with many classes of compounds, an exemplary listing including: $C_2$-$C_{30}$ unsaturated fatty acids; $C_2$-$C_{30}$ unsaturated fatty oils; esters derived from the reaction of $C_1$-$C_{20}$ alcohols with unsaturated $C_2$-$C_{30}$ unsaturated fatty acids; $C_2$-$C_{20}$ polyolefins; $C_4$-$C_{20}$ polydiolefins; $C_8$-$C_{20}$ copolymers derived from polyolefins and vinyl aromatics; and $C_4$-$C_{30}$ alkylated phenols.

In a more preferred embodiment, the classes would include: $C_8$-$C_{30}$ unsaturated fatty acids; $C_8$-$C_{30}$ unsaturated fatty oils; esters derived from the reaction of $C_4$-$C_{20}$ alcohols with unsaturated $C_8$-$C_{30}$ fatty acids; $C_4$-$C_{18}$ polyolefins; $C_4$-$C_{18}$ polydiolefins; $C_8$-$C_{20}$ copolymers derived from polyolefins and vinyl aromatics; and $C_8$-$C_{20}$ alkylated phenols.

The nitrating agent can be nitric acid or nitrogen dioxide gas. When nitric acid is used as the nitrating agent, various concentrations ranging from 30% to 70% are useful in this invention.

Fatty oils suitable for the nitration have a certain degree of unsaturation or some double bonds in their hydrocarbon chains and include animal fats, vegetable oils such as soybean oil, corn oil, canola oil, castor oil, tall oil, and all similar unsaturated triglycerides.

Synthetic esters are normally derived from reacting various alcohols such methanol, butanol, 2-ethylhexanol, trimethylolpropane, pentaerythritol, sorbitol, and the like with fatty acids such as oleic acid, tall oil fatty acid, linoleic acid, linolenic acid, palmitoleic, arachidonic acid and mixtures thereof.

Polyalkenes useful in this invention are preferably polybutenes or polyisobutylenes with molecular weights ranging from 300 to 4500, with 300 to 1000 preferred. Also suitable for nitration are the polymers of other alkenes or $C_2$-$C_6$ olefins such as polyethylenes, polypropylenes, polypentenes, polyhexenes, poly(methyl-2-butene), poly(ethyl-1-butene) and mixtures and blends thereof as well as polydienes, e.g., polybutadiene and polyisoprene and blends thereof.

Copolymers useful in this invention can have terminal or internal double bonds of $C_8$ to $C_{20}$ chain lengths being preferred. The polymers can be either straight or branched chain, e.g., poly(styrene butadiene), and the like, as well as mixtures and blends thereof.

The nitrating agents can be commercial nitric acid with 70% strength which can be used at 70% or be diluted further with water to 30%. The anhydrous form of nitric acid, known as nitrogen dioxide gas ($N_2O_4$) can also be used in place of nitric acid.

No catalyst was used in any nitration processes for making the novel extreme-pressure additives useful in this invention.

To distinguish the nitro-compounds, it is noted that there are similar but different nitrogen-containing chemicals, namely nitrite and nitrates. Nitrous acid ($HNO_2$) can be esterified with alkyl alcohols to yield nitrites which contain C—O bonds and the final functional group of nitrites can be schematically described as —C—O—N=O. Nitric acid ($HNO_3$) can be esterified with the same alcohols to yield nitrates which also contain C—O bonds and their functional groups can be described as —C—O—$NO_2$. On the other hand, nitric acid can undergo the electrophilic substitution or via free radical reaction to form nitro compounds which contain C—N bonds and of which the functional groups can be described as —C—$NO_2$.

The nitration reaction to render the nitro compounds used in this invention can be generalized as follows:

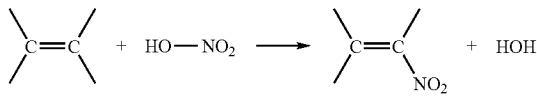

The completion of the nitration reaction can be observed by monitoring the nitro functional group using Fourier Transform Infra-Red ("FTIR"), or by monitoring the decreasing acidity of the reacting medium, or by measuring the amount of water collected which will come from two sources, the 30% water existing in the starting 70% nitric acid from the beginning and the water generated as the by-product of the nitration process. This collected water is measured and tabulated as the percent of nitric acid charged. Theoretically, the total water collected is calculated to equal to 50% of the initial nitric acid charge. However, the yield of the nitration reaction will be slightly less than the theoretical yield due to the loss of the starting raw materials. Some nitric acid will also be lost as the gases of oxides of nitrogen, and some nitrated organic compounds will be lost due to depolymerization or breaking down of hydrocarbon chains due to free radical degradation.

Two nitration methods are used and being described here, one is carried out at 70° C. while the other at 110° C. Also, various molar ratios between nitric acid and nitrated organics, i.e., various degrees of nitration are employed to demonstrate the great flexibility of the nitration method and broaden its scope. The charge of 70% nitric acid is not calculated based on the molecular weight of the nitrated organics but rather based on its unsaturation content or the amount of double bonds existing on the molecular chains. In some instances, the starting compounds become fully nitrated, but in most cases, the degree of nitration is preferred to be at approximately between 35-50% of the degree of unsaturation due to the exothermic nature of nitration and also due to the accelerated degradation caused by such a strong oxidizing agent as concentrated nitric acid.

Typically, at 70° C., a compound which is to be nitrated is selected from fatty oils, PIB, olefins, or alkylated phenols and is charged along with 70% nitric acid. The reacting medium is then heated to 70° C., held at that temperature for 6-8 hours. Subsequently the temperature is slowly increased to 120° C. The batch is held there for about one hour before being cooled to 80° C. Air or nitrogen is then introduced to blow out and remove essentially all entrapped water, which is collected in a Dean-Stark trap, to render a final product. Alternatively, vacuum can be applied for a similar purpose.

If the nitration is carried out at 110° C. or higher, the initial starting organic is heated to 110° C., followed by the addition of a pre-measured amount of 70% nitric acid (which is added slowly) with some cooling to maintain the reacting medium at 100-120° C. After all the nitric acid is charged, the batch is then slowly heated to 120° C., and held at that temperature for about one hour before gas blowing is introduced to remove the water by-product.

The invention is now described in more detail with reference to the following non-limiting examples.

EXAMPLE #1

To a three-necked round bottom flask, equipped with a thermometer, stirring bar, Dean-Stark trap, gas sparger, and a condenser, 89.0 g (0.100 mole) of refined soybean oil and 16.1 g (0.179 mole) of 70% nitric acid were charged The batch was heated to and maintained at 25-140° C., preferably at 60-120° C., more preferably at 70° C. for eight hours. Subsequently the temperature of the reaction was slowly increased to 100° C. The batch was maintained at 100° C. for two hours before cooling to 80° C. The batch was air-blown to remove essentially all entrapped water. A total of 8.0 g water was collected. The total weight loss was 8.7 g or 54% based on the weight of the nitric acid charge. The final yield was 96.5 g of dark brown fluid which FTIR at 1551 cm$^{-1}$ indicated contained the nitro group (C—NO$_2$) The total nitric acid charge amounted to 18% by the weight of the starting organic

EXAMPLE #2

To a three-necked round bottom flask, equipped with a thermometer, stirring bar, Dean-Stark trap, gas sparger, and a condenser, 50.0 g (0.056 mole) of refined soybean oil and 13.2 g (0.147 mole) of 70% nitric acid were charged. The batch was heated to and maintained at 70° C. for eight hours. Subsequently the temperature of the reaction was slowly increased to 100° C. The batch was maintained at 100° C. for two hours before cooling to 80° C. Finally, the batch was air-blown or vacuum applied to remove essentially all entrapped water. A total of 6.6 g water was collected. The total weight loss was 11.4 g or 57% based on the weight of the nitric acid charge. The final yield was 55.6 g of dark brown fluid which FTIR at 1551 cm$^{-1}$ indicated contained the nitro group (C—NO$_2$) The total nitric acid charge amounted to 26% by the weight of the starting organic.

EXAMPLE #3

To a three-necked round bottom flask, equipped with a thermometer, stirring bar, Dean-Stark trap, gas sparger, and a condenser, 50.0 g (0.056 mole) of refined soybean oil and 20.0 g (0.222 mole) of 70% nitric acid were charged. The batch was heated to and maintained at 70° C. for eight hours. Subsequently, the temperature of the reaction was slowly increased to 100° C. The batch was maintained at 100° C. for two hours before cooling to 80° C. The batch was air-blown or vacuum applied to remove essentially all entrapped water. A total of 10.0 g water was collected. The total weight loss was 11.4 g or 57% based on the weight of the nitric acid charge. The final yield was 58.6 g of dark brown fluid which FTIR at 1151 cm$^{-1}$ indicated contained the nitro group (C—NO$_2$) The total nitric acid charge amounted to 40% by the weight of the starting organic.

EXAMPLE #4

To a three-necked round bottom flask, equipped with a thermometer, stirring bar, Dean-Stark trap, gas sparger, and a condenser, 53.0 g (0.059 mole) of FL-216 (Dover Chemical's synthetic esters of trimethylol propane and oleic acid) was added. The batch was heated to 110° C. and 5.3 g (0.059 mole) of 70% nitric acid was charged slowly to keep the temperature between 100-120° C. After all nitric acid was added, the batch was maintained at 110° C. for two hours before cooling to 80° C. The batch was air-blown or vacuum applied to remove essentially all entrapped water. A total of 2.6 g water was collected. The total weight loss was 2.8 g or 53% based on the weight of the nitric acid charge. The final yield was 55.5 g of light brown fluid which FTIR at 1551 cm$^{-1}$ indicated contained the nitro group (C—NO$_2$). The total nitric acid charge amounted to 10% by the weight of the starting organic

EXAMPLE #5

To a three-necked round bottom flask, equipped with a thermometer, stirring bar, Dean-Stark trap, gas sparger, and a condenser, 61.6 g (0.069 mole) of FL-216 (Dover Chemical's synthetic esters of trimethylol propane and oleic acid) was added The batch was heated to 110° C. and 9.2 g (0.102 mole) of 70% nitric acid was charged slowly to keep the temperature between 100-120° C. After all nitric acid was added, the batch was maintained at 110° C. for two hours before cooling to 80° C. The batch was air-blown or vacuum applied to remove essentially all entrapped water A total of 4.6 g water was collected The total weight loss was 4.8 g or 52% based on the weight of the nitric acid charge. The final yield was 65.8 g of light brown fluid which FTIR at 1551 cm$^{-1}$ indicated contained the nitro group (C—NO$_2$) The total nitric acid charge amounted to 15% by the weight of the starting organic.

EXAMPLE #6

To a three-necked round bottom flask, equipped with a thermometer, stirring bar, Dean-Stark trap, gas sparger, and a condenser, 50.9 g (0.057 mole) of FL-216 (Dover Chemical's synthetic esters of trimethylol propane and oleic acid) was added. The batch was heated to 110° C. and 13.2 g (0.147 mole) of 70% nitric acid was charged slowly to keep the temperature between 100-120° C. After all nitric acid was added, the batch was maintained at 110° C. for two hours before cooling to 80° C. The batch was air-blown or vacuum applied to remove essentially all entrapped water. A total of 6.6 g water was collected. The total weight loss was 7.1 g or 54% based on the weight of the nitric acid charge. The final yield was 56.9 g of light brown fluid which FTIR at 1551 cm$^{-1}$ indicated contained the nitro group (C—NO$_2$) The total nitric acid charge amounted to 26% by the weight of the starting organic.

EXAMPLE #7

To a three-necked round bottom flask, equipped with a thermometer, stirring bar, Dean-Stark trap, gas sparger, and a condenser, 86.1 g (0.287 mole) of polyisobutylene (MW avg.=300) and 25.8 g (0.287 mole) of 70% nitric acid were charged The batch was heated to and maintained at 70° C. for eight hours. The temperature of the reaction was slowly increased to 100° C. and maintained at that temperature for two hours before cooling to 80° C. The batch was air-blown or vacuum applied to remove essentially all entrapped water. A total of 12.9 g water was collected The total weight loss was 17.3 g or 67% based on the weight of the nitric acid charge The final yield was 94.5 g of dark yellow fluid which FTIR at 1151 cm$^{-1}$ indicated contained the nitro group ($C-NO_2$) The total nitric acid charge amounted to 30% by the weight of the starting organic.

EXAMPLE #8

To a three-necked round bottom flask, equipped with a thermometer, stirring bar, Dean-Stark trap, gas sparger, and a condenser, 136.3 g (0.136 mole) of polyisobutylene (MW avg.=1000) and 13.8 g (0.153 mole) of 70% nitric acid was charged. The batch was heated to and maintained at 70° C. for eight hours The temperature of the reaction was slowly increased to 100° C. and maintained at that temperature for two hours before cooling to 80° C. The batch was air-blown or vacuum applied to remove essentially all entrapped water. A total of 6.9 g water was collected The total weight loss was 8.1 g or 59% based on the weight of the nitric acid charge. The final yield was 142.0 g of light yellow fluid which FTIR at 1551 cm$^{-1}$ indicated contained the nitro group ($C-NO_2$). The total nitric acid charge amounted to 10% by the weight of the starting organic.

EXAMPLE #9

To a three-necked round bottom flask, equipped with a thermometer, stirring bar, Dean-Stark trap, gas sparger, and a condenser, 63.8 g (0.253 mole) of $C_{18}$ alpha-olefin was charged The batch was heated to 110° C. and 22.7 g (0.252 mole) of 70% nitric acid was charged slowly to keep the temperature between 100-120° C. After all nitric acid was added, the batch was maintained at 110° C. for two hours before cooling to 80° C. The batch was air-blown or vacuum applied to remove essentially all entrapped water. A total of 11.3 g water was collected The total weight loss was 13.1 g or 58% based on the weight of the nitric acid charge. The final yield was 73.2 g of light brown fluid which FTIR at 1551 cm$^{-1}$ indicated contained the nitro group ($C-NO_2$). The total nitric acid charge amounted to 35% by the weight of the starting organic.

EXAMPLE #10

To a three-necked round bottom flask, equipped with a thermometer, stirring bar, Dean-Stark trap, gas sparger, and a condenser, 77.2 g (0.271 mole) of oleic acid was charged. The batch was heated to 110° C. and 17.7 g (0.197 mole) of 70% nitric acid was charged slowly to keep the temperature between 100-120° C. After all nitric acid was added, the batch was maintained at 110° C. for two hours before cooling to 80° C. The batch was air-blown or vacuum applied to remove essentially all entrapped water. A total of 8.8 g water was collected. The total weight loss was 9.9 g or 56% based on the weight of the nitric acid charge. The final yield was 84.9 g of dark brown fluid which FTIR at 1551 cm$^{-1}$ indicated contained the nitro group ($C-NO_2$) The total nitric acid charge amounted to 23% by the weight of the starting organic.

EXAMPLE #11

To a three-necked round bottom flask, equipped with a thermometer, stirring bar, Dean-Stark trap, gas sparger, and a condenser, 100.0 g (0.457 mole) of nonyl phenol was charged. At room temperature, 35.0 g (0.167 mole) of 30% nitric acid was charged slowly to keep the temperature below 100° C. After all nitric acid was added, the batch was maintained at 90° C. for two hours before cooling to 80° C. The batch was air-blown or vacuum applied to remove essentially all entrapped water A total of 26.1 g water was collected The final yield was 106.3 g of dark brown fluid which FTIR at 1551 cm$^{-1}$ indicated contained the nitro group ($C-NO_2$): The total nitric acid charge amounted to 15% by the weight of the starting organic.

Except the nitration of nonyl phenol cited in the last example, all the results obtained from the above-illustrated laboratory batches were tabulated below:

TABLE I

Nitration of organic compounds

| Raw materials ("RM") | RM (g) | RM (moles) | Nitric acid 70% (g) | Nitric Acid (moles) | Wt Loss (%) | Water collected (g) | Yield (g) |
|---|---|---|---|---|---|---|---|
| Soybean oil | 89.0 | 0.100 | 16.1 | 0.179 | 54 | 8.0 | 96.5 |
| Soybean oil | 50.0 | 0.056 | 20.0 | 0.222 | 57 | 10.0 | 58.6 |
| Soybean oil | 50.0 | 0.056 | 13.2 | 0.147 | 57 | 6.6 | 55.6 |
| FL216 | 53.0 | 0.059 | 5.3 | 0.059 | 53 | 2.6 | 55.5 |
| FL216 | 61.6 | 0.069 | 9.2 | 0.102 | 52 | 4.6 | 65.8 |
| FL216 | 50.9 | 0.057 | 13.2 | 0.147 | 54 | 6.6 | 56.9 |
| PIB (MW$_{300}$) | 86.1 | 0.287 | 25.8 | 0.287 | 67 | 12.9 | 94.5 |
| PIB (MW$_{1000}$) | 136.3 | 0.136 | 13.8 | 0.153 | 59 | 6.9 | 142.0 |
| $C_{18}$ olefin | 63.8 | 0.253 | 22.7 | 0.252 | 58 | 11.3 | 73.2 |
| Oleic acid | 77.2 | 0.271 | 17.7 | 0.197 | 56 | 8.8 | 84.9 |

The nitro compounds of Table II were evaluated as extreme-pressure additives, and the results summarized in Table III.

TABLE II

Nitro Compounds And Others Evaluated As EP Additives

| Source | Description | Abbreviation |
|---|---|---|
| Example #1 | Nitro soybean oil | Nitro Soy |
| Example #5 | Nitro synthetic ester | Nitro FL216 |
| Example #7 | Nitro polyisobutylene | Nitro PIB |
| Example #9 | Nitro olefin | Nitro $C_{18}$ |
| Example #10 | Nitro oleic acid | Nitro OA |
| Example #11 | Nitro nonyl phenol | Nitro NP |
| Commercial | 1-Nitropropane | Nitropropane |
| Commercial | 2-Ethylhexyl nitrate | EH Nitrate |
| Dover Chemical | Chlorinated olefin (57% Cl) | X1057 |
| Dover Chemical | Sulfurized Fat (18% S) | Sulfurized Fat |
| Dover Chemical | Sulfurized Olefin (40% S) | Sulfurized $C_{14}$ |

The above-tabulated additives were evaluated in our laboratory using the lab-scaled tapping tester called Microtap II G8, distributed by Microtap USA, Inc. The EP additives were evaluated at 10 wt.% in 100 ml sec-naphthenic oil. Holes were pre-drilled on the steel or stainless steel work-pieces. A series of tapping were done through these predrilled holes at 300 RPM for stainless steel parts and at 450 RPM for regular steel parts. While the tap bit penetrated a 15 mm depth, all data points for torques which were generated due to friction were automatically recorded by the Microtap computer software, an average value was calculated.

In case of steel, this average torque for a nitro extreme-pressure additive or the "tested" torque was compared to the "standard" torque value obtained from a series of tapping done with the base oil alone without any extreme-pressure additive added. This average torque value associated with the pure base oil was served as a standard reference. From the ratio of the tested torque and standard torque, a tapping efficiency was calculated by taking standard torque divided by the tested torque times 100%. If an experimental EP additive generated less torque, it would receive a tapping efficiency of greater than 100% which indicated that it performed well as a lubricating additive. The higher the tapping efficiency, the better the extreme-pressure additive performed. The standard was assigned a 100% tapping efficiency. A better performance than the standard run would result in greater than 100% and vice versa. Due to the repeatability of this tapping test, a difference greater than 3% in tapping efficiency was considered as statistically significant.

The tabulated data obtained with Microtap Tester on steel is summarized in Table III.

TABLE III

Microtap Tapping Efficiency on Nitro EP Additives
450 RPM, 15 mm depth, Steel, 10 wt. % in oil

| Extreme Pressure Additive Sample | Tapping Efficiency |
| --- | --- |
| No additive (Standard) | 100% |
| X1057 (57% Cl) | 122% |
| Sulfurized Fat (18% S) | 133% |
| Sulfurized Olefin (40% S) | 123% |
| 2-EH Nitrate | 124% |
| Nitropropane | 129% |
| Nitro Soy | 133% |
| Nitro FL216 | 130% |
| Nitro $C_{18}$ | 127% |
| Nitro PIB | 126% |
| Nitro NP | 123% |

Examining closely the tabulated data, it is seen that all tested extreme-pressure additives performed better than the standard which is 100% based oil without any additive. Comparing to the chlorinated olefin, namely Dover's X-1057, all performed equally well or better. The nitro compounds derived from soybean oil and synthetic ester appeared to be slightly better than the chlorinated olefin as the extreme-pressure additive on steel. The commercial low molecular weight 1-nitropropane performed well as expected because of its —C—$NO_2$ group. The commercial 2-ethylhexyl nitrate, the ester of nitric acid and 2-ethyl hexanol also performed well on tapping steel parts.

The same Microtap runs tabulated in Table III were repeated using stainless steel bars instead of steel. The runs were conducted at slower speed of 300 RPM instead of 450 RPM. All additives again were tested at 10 weight percent level in oil. This time, the chlorinated olefin blend was served as the standard. The results were summarized and tabulated in Table IV.

TABLE IV

Microtap Tapping Efficiency on Nitro EP Additives
300 RPM, 15 mm depth, Stainless Steel, 10 wt. % in oil

| EP Additive Sample | Tapping Efficiency % |
| --- | --- |
| No additive | (tap bit seized) |
| X1057 (57% Cl) (Standard) | 100% |
| Sulfurized Fat (18% S) | (tap bit seized) |
| Sulfurized Olefin (40% S) | (tap bit seized) |
| 2-EH Nitrate | (tap bit seized) |
| Nitropropane | 98% |
| Nitro Soy | 105% |
| Nitro FL216 | 103% |
| Nitro $C_{18}$ | 100% |
| Nitro PIB | 99% |
| Nitro NP | 100% |

The run with chlorinated olefin or X-1057 was served as the standard with a 100% efficiency for calculating the tapping efficiencies because no tapping torque could be recorded with the run of pure oil (no additive) as the tap bit was seized up inside the pre-drilled holes of stainless steel work pieces. It is evident from the table that all nitro compounds fared equally well or slightly better than the chlorinated paraffin. Again nitro esters such as nitro soybean or nitro synthetic esters performed the best. All nitro hydrocarbons demonstrated to be adequate replacements for chlorinated extreme-pressure in processing stainless steel Contrarily, both sulfurized additives, fat or non-fat, did not do as well with stainless steel as they did with regular steel. That is the reason why all metal processing involving stainless steel or non-steel alloys such as nickel-based and titanium-based based have traditionally always required the presence of chlorine. Comparing N-containing additives, nitro extreme-pressure additives that include the subject of this invention and the commercial 1-nitropropane (hydrocarbons with C—N bonds) in comparison to 2-ethylhexyl nitrate (a hydrocarbon with C—O bonds,) it appears the nitro compounds as a class performed well as the extreme-pressure additive for both stainless and regular steel while nitrate is not effective in processing stainless steel.

After testing with the lab-scaled Microtap tester, the nitro extreme-pressure additive derived from soybean oil was selected to undergo an industrial-scaled precision tapping with a Bridgeport CNC machine (CNC stands for Computer Numerical Control.) As its name indicated this CNC machines can be used to carry out both precision drilling and tapping on a work pieces. All operations were automated and programmed in advance. The work piece was a steel or stainless steel panel 6"(15.25 cm)×3"(7.62 cm) and ¾"(1.91 cm) thick, on which 400 holes were drilled, then the same holes were subsequently tapped. A good lubricant or fluid would drill and tap all 400 holes on the same panel. An inadequate lubricant or cutting fluid would failed immediately with the first tap or soon later after few holes were tapped.

The following results in Table V demonstrate the nitro extreme-pressure additives of this invention, the novel additives which can replace both chlorinated and sulfurized extreme-pressure additives in processing metals.

TABLE V

Formulas of Cutting Fluids used in CNC Drilling & Tapping
Condition: 300 RPM, 400 Holes Maximum, Stainless Steel

| Components | Formula I | Formula II | Formula III | Formula IV |
|---|---|---|---|---|
| Sulfurized Fat (26.5% S) | 12.7% | 12.7% | 17.7% | — |
| Chlorinated paraffin (53% Cl) | 5.0% | — | — | — |
| Nitro soybean (Example #1) | — | 5.0% | — | 17.7% |
| Lard oil | 3.5% | 3.5% | 3.5% | 3.5% |
| sec-naphthenic oil | 78.8% | 78.8% | 78.8% | 78.8% |
| RESULTS: | | | | |
| Total holes tapped | 400 | 400 | 5 (tap bit broken) | 400 |

The above-cited results confirmed once again the vital role of chlorinated extreme-pressure additives in the processing of tough metals such as stainless steel. Again, the sulfurized extreme-pressure additive was not effective, probably due to the non-reactivity of the sulfurized additive toward metallic surfaces which are low in iron such as stainless steel as illustrated by the compositional analysis provided in Table VI for typical compositions of industrial special low-iron or non-iron alloys Conversely, nitro extreme-pressure additives such as nitro soybean oil not only could replace chlorinated compounds in processing stainless steel as shown, but also could replace sulfurized additives in cutting fluid.

Finally, the nitro soybean oil was chosen to represent this novel class of extreme-pressure additives in a cutting fluid in a industrial field application. A commercial cutting fluid which was successful in processing stainless and all special alloys tabulated in Table VI was chosen to be the standard fluid to make metal parts using a full-industry scaled Acme-Gridley Screw Machine. This fluid was then modified with all chlorinated extreme-pressure additives taken out and replaced with nitro soybean oil of Example #1. Both fluids performed equally well in this application with all three metal composites: stainless steel, titanium-based, and nickel-based alloys.

TABLE VI

Typical composition of Low-Steel or non-Steel Special Alloys

| Stainless Steel (A286) | Titanium-Based Alloy | Nickel-Based Waspalloy | Nickel-Based Inconel |
|---|---|---|---|
| C = 0.08% | C = 0.08% | C = 1.0% | C = 0.1% |
| Mn = 2.0% | N = 0.05% | Mn = 0.5% | Mn = 1.0% |
| Si = 1.0% | O = 0.4% | S = 0.02% | S = 0.01% |
| Cr = 13-16% | H = 0.01% | Si = 0.75% | Si = 0.5% |
| Ni = 24-27% | Ti = Bal | Cr = 18% | Cr = 21-25% |
| Mo = 1-2% | Fe = 0.5% | Ni = Bal | Ni = 58-63% |
| V = 0.1-0.5% | | Mo = 3.5% | Co = 1.0% |
| Ti = 1.9-2.3% | | Cu = 0.1% | Al = 1% |
| Al = 0.35% | | Co = 12% | |
| Fe = Bal | | Ti = 2.6% | |
| | | Al = 1% | |
| | | Fe = 2% | |
| | | Zr = 0.1% | |

This invention describes a method to synthesize a novel class of nitrated extreme-pressure additives used in lubricating oils. This invention also describes a method to synthesize this class of additives by reacting nitric acid with fatty or synthetic raw materials such as triglycerides, methyl or synthetic esters including water-dispersible esters, fatty or synthetic alcohols including polyglycols, fatty acids such as oleic acid, tall oil fatty acid or unsaturated carboxylic acids, and with olefins.

What has been shown is that nitric acid can react with: (a) animal fat or glycerides from animal fat such as lard, pigskin grease, chicken fat, cod or fish oil, sheep fat, blubber, etc.; (b) vegetable oils including oils from oilseeds, such as cashew, castor bean, castor oil, flax seed—linseed oil, grape seed—grape seed oil, hemp (cannabis), mustard olives and olive pits—olive oil, poppy seeds—poppyseed oil, rapeseed, canola (cultivar of rapeseed), safflower, sesame seed, sunflower, as well as other vegetable oils such as almond, apricot, argan, avocado, corn (maize)—corn oil, cotton plant seed—cottonseed oil, coconut—coconut oil, fusarium—actually a fungus, hazelnut, neem oil, palm—palm oil—from the fruit of the African palm tree, palm kernel oil—from the seed of the African palm tree, peanut—peanut oil, pumpkin seed, rice bran, soybean—soybean oil is commonly marketed as "Vegetable Oil", walnut, canola, soybean oil, corn oil, etc.; (c) olefins, internal or alpha, short chain or polymers including polyalkylene oxides, polyalkylenes, polyalkylated aromatics, etc.; and (d) unsaturated hydrocarbons, including alkenes, arylalkyls, alkylaryls, etc.

High rosin fatty acids may be substituted in whole or in part for non-high rosin fatty acids used in embodiments described elsewhere herein. It is recognized that sources of $C_6$-$C_{24}$ fatty acids include, but are not limited to, those obtained from natural sources such as animal tallows and greases, vegetable, coconut, palm, marine oils, etc. Such acids may also be produced synthetically from petroleum sources. For example, fatty acids may be produced by oxidation of hydrocarbons.

This invention describes the reactions and reactant yields between nitric acid and fatty compounds in which nitric acid charge can range from 0.1 mole to 3.0 mole for each mole of triglycerides or 0.1 to 1.0 mole of nitric acid for each mole of fatty acids/esters, alcohols, or olefins.

What is also known is that nitric acid can oxidize essentially all organic matter, particularly hydrocarbons, and therefore, this invention extends to any chemical that contains a hydroxyl group, hydroalkyl chain, or alkyl group that can be reacted with nitric acid to provide a nitrated additive of this invention. These nitrated hydrocarbons are useful as the extreme-pressure additives of the instant invention.

This invention describes the use of the above-mentioned nitrated extreme-pressure additives in a lubricant formulation for metal processing applications, for an industrial lubricating formula or other applications requiring the use of a lubricant and which are an effective replacement for the currently available chlorinated compounds and usable with stainless steel processing applications.

These nitrated additives can be combined with other extreme-pressure or lubricity additives and be used in straight oil formulations or even in water-based, soluble oil formulations. Other extreme-pressure additives can be combined with the nitrated additives, and can include blends with chlorine, sulfur and phosphorus compounds in which case the nitrated additive acts as a partial replacement for traditional lubricants. Alternatively, the nitrated additives can be used as blends and as either a total or partial replacement for traditional lubricants.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the invention is by way of example, and the scope of the invention is not limited to the exact details shown or described.

This invention has been described in detail with reference to specific embodiments thereof, including the respective best modes for carrying out each embodiment. It shall be understood that these illustrations are by way of example and not by way of limitation.

What is claimed is:

1. A process of using an extreme pressure additive with steel, stainless steel, metals or alloys containing titanium, chromium or nickel, which comprises the steps of:
    nitrating at least one $C_{20}$-$C_{30}$ alkylated phenol
    wherein said $C_{20}$-$C_{30}$ alkylated phenol is selected from the group consisting of $C_{20-30}$ alkyl alcohols, $C_{20-30}$ aryl alcohols, $C_{20-30}$ arylakyl alcohols, $C_{20-30}$ alkylaryl alcohols or esters thereof,
    adding said at least one nitrated moiety to a lubricating oil or grease to form said extreme pressure additive,
    said extreme pressure additive reacting with at least one metal selected from the group consisting of steel, stainless steel, metals and alloys containing titanium, chromium or nickel thereof via chemi-adsorption to form a sacrificial coating on said steel, stainless steel, metals or alloys containing titanium, chromium or nickel;
    adding at least one non-chlorine containing moiety to said oil-based lubricant, a combination of said non-chlorine containing moiety and said nitrated moiety improving a performance of said extreme-pressure, water-dispersible additive in at least one physical characteristic associated with cutting applications when compared to using said additive without said combination and further wherein said non-chlorine containing moiety is selected from the group consisting of a sulfur-containing moiety and a phosphorus-containing moiety.

2. The process of claim 1 wherein said at least one nitrated moiety is a minor amount and said oil or grease is a major amount.

3. A process of using an extreme-pressure additive with steel, stainless steel, metals or alloys containing titanium, chromium or nickel, as at least a partial replacement for chlorinated extreme-pressure additives which comprises the steps of:
    nitrating soybean oil,
    adding said nitrated soybean oil to a lubricating oil or grease to form said extreme-pressure additive,
    said nitrated soybean extreme-pressure additive reacting with at least one metal selected from the group consisting of steel, stainless steel, special metals and alloys thereof via chemi-adsorption to form a sacrificial coating on said steel, stainless steel, metals or alloys containing titanium, chromium or nickel,
    said nitrated soybean extreme-pressure additive performing at least as well as said chlorinated extreme-pressure additive in a microtap tapping efficiency test associated with cutting applications.

4. A process of using an extreme-pressure additive with steel, stainless steel, metals or alloys containing titanium, chromium or nickel, as at least a partial replacement for chlorinated extreme-pressure additives which comprises the steps of:
    nitrating a reaction product of an ester blend of a polyol and an unsaturated fatty acid,
    adding said nitrated ester blend to a lubricating oil or grease to form said extreme pressure additive,
    said nitrated ester blend extreme-pressure additive reacting with at least one metal selected from the group consisting of steel, stainless steel, special metals and alloys thereof via chemi-adsorption to form a sacrificial coating on said steel, stainless steel, metals or alloys containing titanium, chromium or nickel,
    said nitrated ester blend extreme-pressure additive performing at least as well as said chlorinated extreme-pressure additive in a microtap tapping efficiency test associated with cutting applications.

5. A process of using an extreme-pressure additive with steel, stainless steel, metals or alloys containing titanium, chromium or nickel, as at least a partial replacement for chlorinated extreme-pressure additives which comprises the steps of:
    nitrating an unsaturated fatty acid,
    adding said nitrated fatty acid to a lubricating oil or grease to form said extreme pressure additive,
    said nitrated fatty acid extreme-pressure additive reacting with at least one metal selected from the group consisting of steel, stainless steel, special metals and alloys thereof via chemi-adsorption to form a sacrificial coating on said steel, stainless steel, metals or alloys containing titanium, chromium or nickel,
    said nitrated fatty acid extreme-pressure additive performing at least as well as said chlorinated extreme-pressure additive in a microtap tapping efficiency test associated with cutting applications.

* * * * *